(12) United States Patent
Rostro et al.

(10) Patent No.: US 9,663,734 B2
(45) Date of Patent: May 30, 2017

(54) SOLUTIONS OF ALLOTROPES OF CARBON AND METHODS OF MAKING AND USING THE SAME

(75) Inventors: Bertha Rostro, Houston, TX (US); Mehdie Kohanloo, Houston, TX (US)

(73) Assignee: BCR Science PLLC, Dallas, TX (US)

( * ) Notice: Subject to any disclaimer, the term of this patent is extended or adjusted under 35 U.S.C. 154(b) by 226 days.

(21) Appl. No.: 13/078,930

(22) Filed: Apr. 2, 2011

(65) Prior Publication Data

US 2012/0251521 A1 Oct. 4, 2012

(51) Int. Cl.

| | | |
|---|---|---|
| A61K 33/44 | (2006.01) |
| C10L 1/18 | (2006.01) |
| C10L 1/188 | (2006.01) |
| C10L 1/182 | (2006.01) |
| C09D 1/00 | (2006.01) |
| C08K 3/04 | (2006.01) |
| C09K 5/04 | (2006.01) |
| H01G 9/022 | (2006.01) |
| C09K 5/00 | (2006.01) |
| H01B 1/24 | (2006.01) |
| C09K 9/00 | (2006.01) |
| C09K 3/00 | (2006.01) |
| G03F 7/004 | (2006.01) |
| B82Y 30/00 | (2011.01) |
| C10L 1/10 | (2006.01) |
| C09D 11/52 | (2014.01) |
| C09D 7/00 | (2006.01) |
| C01B 31/02 | (2006.01) |
| C01B 31/04 | (2006.01) |
| C09C 1/48 | (2006.01) |
| C09C 1/56 | (2006.01) |
| B82Y 40/00 | (2011.01) |
| B01J 35/12 | (2006.01) |
| H01L 39/12 | (2006.01) |
| C10M 125/02 | (2006.01) |
| C11D 3/60 | (2006.01) |
| A61K 47/02 | (2006.01) |
| C09K 3/30 | (2006.01) |
| A61P 35/00 | (2006.01) |
| A61P 31/12 | (2006.01) |
| A61P 31/10 | (2006.01) |
| C10L 1/16 | (2006.01) |
| B82Y 5/00 | (2011.01) |
| C10L 1/12 | (2006.01) |
| C10L 1/185 | (2006.01) |
| H01L 39/00 | (2006.01) |
| H01G 11/54 | (2013.01) |

(52) U.S. Cl.
CPC .............. *C10L 1/10* (2013.01); *B82Y 30/00* (2013.01); *B82Y 40/00* (2013.01); *C01B 31/0273* (2013.01); *C01B 31/0484* (2013.01); *C09C 1/48* (2013.01); *C09C 1/56* (2013.01); *C09D 1/00* (2013.01); *C09D 7/001* (2013.01); *C09D 11/52* (2013.01); *C09K 5/00* (2013.01); *C01P 2004/13* (2013.01); *C10L 1/1208* (2013.01); *C10L 1/1608* (2013.01); *C10L 1/1822* (2013.01); *C10L 1/1824* (2013.01); *C10L 1/1855* (2013.01); *H01G 9/022* (2013.01); *H01G 11/54* (2013.01); *H01L 39/005* (2013.01); *Y02P 20/129* (2015.11)

(58) Field of Classification Search
CPC .......... B82Y 30/00; B82Y 40/00; C09K 5/00; C09D 11/52; C09D 1/00; C09D 7/001; C01B 31/0273; C01B 31/0484; C09C 1/48; C09C 1/56; C10L 1/10; C10L 1/1208; C10L 1/1608; C10L 1/1822; C10L 1/1824; C10L 1/1855; Y02P 20/129; H01L 39/00
USPC ..... 423/445 R, 447.1, 448, 460, 461, 445 B; 977/842, 845, 847
See application file for complete search history.

(56) References Cited

U.S. PATENT DOCUMENTS

| | | |
|---|---|---|
| 5,612,021 A | 3/1997 | Mellul |
| 7,708,903 B2 | 5/2010 | Sievert et al. |
| 2003/0026754 A1 | 2/2003 | Clarke et al. |
| 2005/0112053 A1 | 5/2005 | Clarke et al. |
| 2005/0136079 A1 | 6/2005 | Burangulov et al. |
| 2006/0189822 A1* | 8/2006 | Yoon et al. ............. 560/130 |
| 2009/0317660 A1* | 12/2009 | Heintz et al. ............ 428/688 |
| 2010/0059720 A1* | 3/2010 | Berkei ............. B82Y 30/00 252/511 |
| 2010/0288965 A1 | 11/2010 | Howell et al. |

OTHER PUBLICATIONS

Kim et al., "Individualization of Single-Walled Carbon Nanotubes: Is the Solvent Important?," 2005, Small, vol. 1, Issue 11, pp. 1117-1124.*

(Continued)

*Primary Examiner* — Daniel C McCracken

(57) ABSTRACT

Provided herein are compositions comprising solutions or colloids of allotropes of carbon, in particular fullerenes, graphenes or single walled carbon nanotubes (SWNTs or polymers of fullerenes) in solvents selected from terpenes, lactones or fatty acid or terpene alcohols. The carbon allotropes remain in solution following ultrasonication and ultracentrifugation processing. Suitably the solvents are selected from monoterpene cyclic ethers, cyclic terpenes, cyclic triterpenoid species, cyclic triterpenoid steroidal species, or terpene alcohols. The compositions are made by combining the solvents with the allotrope of carbon with cavitation. Methods of using these compositions are also provided.

4 Claims, No Drawings

(56) References Cited

OTHER PUBLICATIONS

Detriche et al., "Application of the Hansen Solubility Parameters Theory to Carbon Nanotubes," 2008, Journal of Nanoscience and Nanotechnology, vol. 8, pp. 6082-6092.*
Besteman, et al., Enzyme-Coated Carbon Nanotubes as Single-Molecule Biosensors, Nano Letters 2003; 3(6): 727-730.*
Margulis, et al., Mechanism of Sonochemical Reactions and Sonoluminescence, High Energy Chemistry 2004; 38(4): 285-294.*

* cited by examiner

SOLUTIONS OF ALLOTROPES OF CARBON AND METHODS OF MAKING AND USING THE SAME

TECHNICAL FIELD AND INDUSTRIAL APPLICABILITY OF THE INVENTION

Methods for solubilizing allotropes of carbon such as fullerenes, graphene, or polymers of fullerenes (i.e. single walled carbon nanotubes (SWNTs)), at milligrams per milliliter (mg/mL) loadings in cyclic terpene, cyclic triterepenes, lactones, fatty acid alcohols, and specific terpene alcohols are provided herein. The methods include combining the carbon allotropes with the indicated solvents which can include processing consisting of cavitation such as ultrasonication, and ultracentrifugation. The methods lead to true solutions that when processed with media such as degassed solvent, fluid, fuel, additive, lubricant, polymer, film, gel, electrolyte, mesoporous material, metal catalyst, fillers, adhesive, paint, ink, dye, or substrate results in compositions that can produce a film, grease, coating, fluid, or other media. Uses include oilenergy, biological, and electrical-thermal applications.

BACKGROUND OF THE INVENTION

Buckminster-Fullerenes are $C_{60}$, they are carbon allotropes, which are spherical molecules, also termed buckyballs, composed entirely of carbon. $C_{60}$ are truncated icosahedrons with a closed-cage structure composed of 20 hexagons and 12 pentagons, and are characterized via mass spectrometry, UV-Visible spectrometry, gas chromatography, and other optical spectroscopy methods. The fullerene $C_{60}$ has a conjugated electronic structure that allows for a high intermolecular interaction. The molecular packing of the crystalline $C_{60}$ structures controls its solvation properties. Aromatic solvents such as polar aromatic hydrocarbons, and terpenes, lactones, fatty acid alcohols, or other molecules with similar conjugated structures and high intermolecular interactions will favor solvation.

Carbon nanotubes, namely single-walled carbon nanotubes (SWNTs) are of the fullerene structural family, and are allotropes of carbon with cylindrical nanostructures, note that these can often have fullerene capped ends. The carbon nanotubes have novel properties due to their 1-dimensional (1-D) and $sp^2$ orbital hybridization, which provides them with chemical bonds that are similar to graphite. The strong van der Waals forces of carbon nanotubes allows them to align into roped structures, with diameters close to 1 nm, leading to a one-atom thick structure that is a graphene cylindrical sheet. Of critical importance is their solvation in solvents that have minimal environmental and human exposure liabilities. While some solvation methods are known these are not suitable for large-scale processing. Most of these solvation methods require density-gradient ultracentrifugation of surfactant wrapped nanotubes. Still other methods use chromatographic, gel electrophoresis, or DNA or macromolecular complexation. Nevertheless current applications of single-walled carbon nanotubes are limited due to their lack of solubility, toxicity, environmental liabilities, and efficient and large-scale processing.

Graphene is the basic structural element of carbon allotropes such as fullerenes and carbon nanotubes, and can be considered a type of flat polycyclic aromatic hydrocarbon. The structure of graphene is a one-atom thick planar sheet of $sp^2$-bonded carbon atoms that are densely packed in a honeycomb crystal lattice. Currently the dispersion of graphene is quite difficult, often requiring chemically processed or unique functionalizations that allow for dispersions in some polar aromatics. Still other chemical modifications are possible following treatment with strong acids leading to oxidation, and exfoliation, and an oxidized graphene structure. However this strongly aggressive chemical processing and caustic use of solvents can present time constraint and human and environmental exposure issues. Still other methods employ hydrogenation of graphene, which alters its chemical and electrical properties. While graphene has many exceptional properties, which are often desirable in electrical and thermal applications, its solubility and time-consuming processing, and functionalization can often limit its use.

A limited number of solvents have been used to dissolve fullerenes, graphene, and polymers of fullerenes such as carbon nanotubes. True solutions of fullerenes, graphene, and SWNTs, can be made from either strong aggressive acids, aromatic halogenated hydrocarbons, or toxic aromatic hydrocarbon based solvents that present human and environmental exposure liabilities.

Terpenes are hydrocarbon solvents resulting from the combination of several isoprene units, these can be monoterpenes, sesquiterpenes, diterpenes, and/or triterpenes, with some being linear, while others being cyclical in nature. Within these groups there are other families and grouped subcategories, these differ based on their structural or chemical functional groups, some of the ones used in this formulation include monoterpene cyclic ethers, terpene alcohols, associated fatty acid alcohols, cyclic terpenes, associated lactones, cyclic triterpenoid saponins, and cyclic triterpenoid steroidal saponins. This disclosure also employs lactones, which are internal cyclic monoesters, and fatty acid alcohols, which are aliphatic carboxylic acids.

DESCRIPTION OF RELATED ART

Colloidal dispersions, emulsions, or other aggregate based solutions have been extensively disclosed and noted in the literature. U.S. Pat. No. 5,612,021; U.S. Pat. No. 7,708,903, and some provisional patents have discussed solubilizing fullerenes into small clusters through the use of aromatic solvents combined with terpene-based solvents for cosmetic or refrigerant use. Previously published terpene and saponin disclosures to formulate SWNTs fail to mention the specific class of terpenes, and/or type of saponins, or specific structural types that were used to provide clustered dispersions, leading to a generic use of terpene, terpenoid, or saponin. This presents a complication, given that there are thousands of terpenes, as such using IUPAC or CAS, or chemical family structural names is desired, and should be required.

Previously published patents or disclosures also do not discuss a process method leading to media of dissolved fullerenes or solutions of fullerenes in cyclic terpenes, where the dissolved solutions or true solutions refer to a lack of aggregates and/or clustering. Some disclosed and published patents have made use of functionalized fullerenes and/or additives such as dispersants, or surfactants, however, while these may increase solubility, these derivatized fullerenes can reduce the conjugation of the molecules and often create steric hindrances leading to decreased reactivities and overall functionalities. The type of saponin dispersants and/or surfactants may also pose an environmental or human exposure liability, very few are nontoxic, which is often not desired. Other patents and journal articles have referred to electrolyte, polar, and/or ionic liquids work quite well to solvate fullerene polymer species such as SWNTs, graphene, and fullerenes, due to their ability to donate ions and/or neutralize ionized molecules enhancing the n-electron density interactions between aromatic molecules and neighbors. This is an electric double layer type interaction, and the drawback to these systems is their environmental and human exposure liabilities, mostly in terms of toxicity.

This work makes use of an accessible surface area (ASA) of the solute, readily available to the solvent. This increased surface area together with the ASA of the van der Waals solids (fullerenes, graphene, SWNTs) will allow some control over the solvation, and colloidal properties of the system. Dispersive forces also become relevant as these are electrostatic in nature, resulting from random charge fluctuations, and not the permanent electrical charges often present in some molecules. Such behavior induces polarization and increased repulsion between two charges. It is therefore the distance of the solvents coupled with the similar intermolecular forces and desired vapor pressure, which is important, not position. This optimal distance is what determines the attraction or repulsion of some solvents and molecules.

Charge resonance stabilized charge distributions, resonance, and delocalization naturally impart aromatic molecules with high stabilities and high intermolecular forces. $C_{60}$, graphene, and SWNT like molecules have short-range screening properties and long-range anti-screening properties due to their dipole and electron confined structures (1-dimensional or 2-dimensional respectively). At very short distances the Coulomb interactions can be screened while at larger distances they are anti-screened. Such behavior induces polarization and increased repulsion between two charges. However, at some optimal distances, if the intermolecular forces are similar and the vapor pressures of the solvent favor cavitation within the ASA this allows for solvation. Under increased temperatures and cavitation then the solvation of the fullerene, SWNTs, and graphene molecules is favored.

SUMMARY OF THE INVENTION

A method for solubilizing allotropes of carbon such as fullerenes, graphene, or polymers of fullerenes (i.e. SWNTs), at milligrams per milliliter (mg/mL) loadings in cyclic terpene, cyclic triterepenes, lactones, fatty acid alcohols, and specific terpene alcohols is provided herein. The methods include combining the carbon allotropes with the indicated solvents which can include processing consisting of cavitation such as ultrasonication, and ultracentrifugation. The ultracentrifugation may be carried out at least at 325,000×g for 1 hour, or 120,000×g for 4 hours or 462,700×g for 1 hour The method leads to a composition that when processed with media produces a film, grease, coating, fluid, or other media. The composition allows for characterization using FTIR, UV-Visible spectroscopies, mass spectrometry, and/or other optical spectroscopic methods to accurately and precisely determine the concentration. Uses include oil-energy, biological, and electrical-thermal applications.

The solubilized solutions of fullerenes, graphene, or polymers of fullerenes (i.e. SWNTs) in either cyclic terpenes, or cyclic triterepenes, or lactones, or fatty acid alcohols, and/or specific terpene alcohols or combinations thereof, underwent ultrasonication and ultracentrifugation processing steps to ensure solubility. The ultracentrifuged, solvated, cluster flee solutions could then be characterized using FTIR, UV-Visible spectroscopies, mass spectrometry, and/or other optical methods to accurately and precisely determine the concentration.

This invention also discusses colloidal dispersions of fullerenes, graphene, or polymers of fullerenes (i.e. SWNTs) in cyclic terpenes, cyclic triterepenes, lactones, fatty acid alcohols, and specific terpene alcohols at weight percent loadings, that underwent processing consisting of ultrasonication, and ultracentrifugation at least 325,000×g that being 48,609 RPM for 1 hour, or 120,000×g that being 29,537 RPM for 4 hours, or a preferred 462,700×g that being 58,000 RPM for 1 hour. Following the ultracentrifugation processing, the colloidal dispersions could undergo optical characterization using FTIR, UV-Visible spectroscopies, mass spectrometry, and/or other optical methods.

Since this invention avoids chemical functionalization, oxidation, or derivitization of the fullerenes, graphene, or polymerized fullerenes (i.e. SWNTs), and/or clustering for the dissolved solutions at the mg/mL loadings this allows for higher enhanced chemical reactivity, meaning electron-donor and molecular packing of solvent-molecule interactions, which allows for true solvation of solvents that have decreased environmental and human exposure liabilities (toxicity).

Colloidal dispersions of fullerenes, graphene, or polymers of fullerenes (i.e. SWNTs) at weight percent loadings, or solutions of 1 mg/mL to 100 mg/mL, of fullerenes, graphene, or polymers of fullerenes; in monoterpene cyclic ethers, terpene alcohols, fatty acid alcohols, cyclic terpenes, cyclic triterpene species, lactones, and/or cyclic triterpenoid steroidal species, or combinations thereof are provided.

Monoterpene cyclic ethers are chosen from: 1, 4 cineole, 1, 8 cineole, cineole, eucalyptol, or combinations thereof. Terpene alcohols or fatty acid alcohols are chosen from: linalool, oleyl alcohol, oleic acid, terpineol, or combinations thereof. Cyclic terpenes are chosen from: α-terpinene, cinene, or combinations thereof. Lactones are chosen from: γ-Dodecalactone, γ-octalactone. Cyclic Triterpenoid saponins used are described as: consisting of a 30-carbon atom hydrophobic core of the Δ12-oleanone type and aglycone sapogenin moiety bound to hydrophilic glucose such as Quillaja Saponin consisting of quillaic acid and glucuronic acid, with a sapogenin content of no less than 10%, with preferred 20-35% sapogenin content, or calendula saponin with an oleanolic acid genin, with a sapogenin content of no less than 10%. Cyclic triterpenoid steroidal saponins used are described as: consisting of at least 27 carbon atoms in cyclic form, and an aglycone sapogenin that is a choline steroid, with a sapogenin content of no less than 10%, with preferred 30-60% sapogenin content, such as *yucca Schidigera* saponin.

Visual inspection of the cyclic terpene, alcohol, lactone, -based solutions will evidence a color change following full dissolution and solvation of fullerene, graphene, fullerene-polymers (i.e. SWNTs). The color of the solvent being clear, and changing to red, purple, maroon, or gray upon solvation of the fullerene, graphene, or fullerene-polymers (i.e. SWNTs). Optical characterization of these color changes which are intrinsic to solvated fullerene, graphene, fullerene-polymer (SWNTs) is evident in spectral features of these solutions, and common to solvents that contain double bonds, C═C in their structure, which likewise is present in the fullerene, graphene, and fullerene-polymers (i.e. SWNTs).

The similar structures of the cyclic terpenes, terpene alcohols, fatty acid alcohols, lactones, cyclic triterpenoid saponins, and cyclic triterpenoid steroidal saponins, to fullerenes, graphene, and fullerene polymers (i.e. SWNTs), their C═C conjugated structures, degree and/or number of conjugated bonds, and strong polarizability is responsible for the increased solvation abilities. Further the conjugated electronic structures of these molecules allows for a high intermolecular interaction for molecular solid crystals. The molecular packing in the crystal lattice and dense mode of the fullerenes, graphene, and fullerene polymers (i.e. SWNTs), allows the crystalline structures to solvate with aromatic solvents such as aromatic hydrocarbons and cyclic terpenes, lactones, fatty acid alcohols, or other molecules that have similar conjugated or high intermolecular interactions, which confer unique electron-donor packing of aromatic molecules. The combination of polarization forces, degree and number of C=C conjugated bonds, intermolecular interactions, allows for greater molecular packing, and controls the solubility values for the fullerenes, graphene, and fullerene-polymers (i.e. SWNTs), which is based on the number of C=C bonds present, and available contact area. This allows for full solvation, which is noted following ultrasonication, and ultracentrifugation processing, yielding true solutions, which allow for optical and mass spectrometry characterization.

In order for solvation to occur in monoterpene cyclic ethers, cyclic terpenes, cyclic triterpenoid species, cyclic triterpenoid steroidal species, terpene alcohols, fatty acid alcohols, lactones, and/or combinations thereof; or hydrocarbon electrolytes, and polar solvents; an accessible surface area (ASA) of the solute must be readily available to the solvent. For van der Waals surfaces such as a fullerenes, graphene, or fullerene polymers (i.e. SWNTs) this solvent ASA must be taken into account in addition to the increased surface area of the molecules. Increased surface areas of carbon-based nanoparticles allows for enhanced storage of ions, radicals, and electrolyte species for any given volume. This increased surface area together with the ASA of the van der Waals solids (fullerenes, graphene, SWNTs) will allow some control over the solvation, and colloidal properties of the system.

Solvents will collide with solutes, thereby changing the energetics of the system. Often this causes temperature changes, which can aid the dipole, dielectric, miscibility, and vapor pressure properties of both the solvents and solute, to enhance solvation. Dispersive forces also become relevant as these are electrostatic in nature, resulting from random charge fluctuations, and not the permanent electrical charges often present in some molecules. Since the collective nature of the aromatic rings confers notoriously strong intermolecular forces between hydrocarbon/graphitic/aromatic species these properties become highly important for colloids and/or solutions.

Charge resonance stabilized charge distributions, resonance, and delocalization naturally impart aromatic molecules with high stabilities and high intermolecular forces. $C_{60}$, graphene, and SWNT like molecules have short-range screening properties and long-range anti-screening properties due to their dipole and electron confined structures (1-dimensional or 2-dimensional respectively). At very short distances the Coulomb interactions can be screened while at larger distances they are anti-screened. Such behavior induces polarization and increased repulsion between two charges. It is therefore the distance of the solvents coupled with the similar intermolecular forces and desired vapor pressure, which is important, not position. This optimal distance is what determines the attraction or repulsion of some solvents and molecules.

The solubility values for the fullerenes, graphene, and fullerene-polymers (i.e. SWNTs), are also based on the number conjugated carbon bonds present, and available contact area. The hydrophobic nature of these molecules, intermolecular forces, density, vapor pressure, and their short versus long-range nature, coupled with density changes, can enhance repulsion or attraction. If the close approach distance is not optimal then repulsion is favored. However, at some optimal distances, if the intermolecular forces are similar and the vapor pressures of the solvent favor the nucleation of the vapor phase. Cavities within the ASA and bubbles will ensue, which favor cavitation processes due to bridging forces, nucleation, and coalescence of cavitation bubbles. This allows for the solvent properties to exceed the long-range van der Waals forces of the solute molecules rendering solvation. Under increased temperatures and cavitation then the solvation of the fullerene, SWNTs, and graphene molecules is favored.

The compositions comprising solutions of a carbon allotrope and a solvent can be combined with media such as fuel, additive, lubricant media. Fuels such as: biofuel, biodiesel, biojet fuel, gasoline fuel, or kerosene may be used. Additives such as: identification dyes, detergents/surfactants, degassed solvents, and/or corrosion inhibitors, biofuel additives, engine oil additives, antifriction agents, anti-wear agents, oil misting additives, synthetic additive, gel additive, or grease additives. Lubricants such as: oil, grease, gel, oil misting lubricant, synthetic oil, synthetic based grease, synthetic based gel, turbocharger lubricant or supercharger lubricant. The compositions may also be combined with thermal fluids such as low temperature heat transfer fluid, heat pump fluid, phase-change fluid, solar collector fluid, parabolic trough fluid, power plant fluid, electrical-thermal energy storage fluids, anti-freeze fluids, or industrial heat transfer fluids. These resulting compositions can be used as heat exchanger media, parabolic trough media, thermal energy storage technology media, electrical-thermal energy storage media.

The compositions may also be combined with polymer and electrolyte media. The polymers may include conductive polymer, semiconductive polymer, polymer fluid, polymer film, polymer thin film, or polymer gel. The electrolyte media may include dye-sensitized fluids, electrolytes, or dye-sensitized electrolytes. These resulting compositions may be used in batteries, capacitors, rectifiers, anodes, cathodes, conductive thin films or fluids or gels, or electronic elements that employ electrochemical devices or dielectrics in electrically conductive solvent systems, or dye-sensitized solar cell electrolyte, ink for jetting or stamping and printing of semiconductive and electroactive polymers, and/or electro-optical coatings, inks or dyes.

The compositions may also be combined with solvents, fillers, adhesives, paints, inks, or dyes and can be used in photovoltaic media. These compositions can be used in liquid crystal display (LCD), electronic ink for reflective or transmitting display in mobile devices and/or solar panel or window, or as window tinting film or paint or ink or dye, or solar powered photovoltaic panel media, or dye-sensitized solar cell media, or electron circuit material.

The compositions may also be combined with electrical or thermal fluids such as electrorheologic, thermophoretic, thermodiffusion, or electrohydrodynamic fluids. These resultant compositions can be used with media such as fluid, gel, or film that is electrically and thermally conductive such that the electrorheologic, thermophoretic, electrohydrodynamic, or magnetohydrodynamic properties are enhanced to produce propellants for electric propulsion, plasma jet fluids, or magnetohydrodynamic propulsion.

The compositions may also be combined with metal oxide, mesoporous carbon, alumina, or silica supported film that houses catalysts such as Pd, Pt, Zn. These compositions may lead to electric or thermal composition media such as superconductive material for thin film or fluid or media or gel, or metal oxide thin film or fluid or media or gel exhibiting superconductivity properties, or hydrogen storage material.

The compositions may be combined with drug delivery or skin permeable agents such as anti-cancer, anti-viral, or anti-fungal drug delivery agent. These compositions may lead to electric or thermal composition media with enhanced electrical and thermal skin conductivity which can enhance skin permeability and that prevents the binding of virus, bacteria, and fungus, thereby preventing penetration, and/or the development of infections.

The compositions may be combined with polymeric or biopolymeric media, such as gelatin, agar. These compositions may be dichroic and/or dichromic gel, fluid, or media, dichroic and/or dichromic waveguide gel, fluid, or media, dichromated and/or dichroic hologram gel, fluid, or media, or electrochromic gel, fluid, or media. Such resultant compositions may be useful electric or thermal composition media for use as dielectric optical coating media for heat sinks, electro-surgical instruments, corona suppression, or media for thermal spray resistance, or media for electrical material such as conductor or insulator, and or media for waveguide such that laser or electrical or magnetic resonance enhancement results.

A lubricant composition results in a fuel or fluid such as an oil misting lubricant, synthetic lubricant, turbocharger lubricant, turbocharger fuel, or synthetic fuel, or supercharger fuel or fluid can be made using compositions provided herein. The lubricants may be formulated by mixing a solute of at least 20 mg/mL sublimed fullerene in a terpene solvent is mixed with at least 16.6% by weight with 73.4% by weight of lubricant or fuel such as high-grade formulated synthetic oil with additives, or biofuel or hydrocarbon fuel with 10 weight % of additives.

A photovoltaic composition for thermal energy storage media such as that used in UV-shielding and transparent-free standing electrochromic films, fluids or gels or media for heat exchange, solar collector media, parabolic trough media, power plant media. The composition may include a solute of 20 mg/mL sublimed fullerene in a terpene solvent, and at least 15% weight gelatin biopolymer in at least 55% weight of $H_2O$ which forms a polyelectrolyte composed of at least 1% weight glacial organic acid such as glacial acetic acid, 7-28% by weight plasticizer such as glycerol, and 1% weight crosslinker such as formaldehyde with electrochromic substrate media such as, but not limited to glass/antimony-doped tin oxide (ATO)/$Nb_2O5$/gelatin-terpene-fulleren/$SnO2$-ATO-$CeO2$-$TiO2$/ATO/glass. The heat transfer and phase-change properties result in electrical and thermally conductive, electrorheologic, thermophoretic, thermodiffusion, electrohydrodynamic, or magnetohydrodynamic properties which allow for electrical-thermal energy storage.

A photovoltaic patterned dye-sensitized transparent carbon SWNT solar cell electrolyte is formed resulting in an electronic element that is a fluid or gel or lubricant or media or thin-film for batteries, capacitors, rectifiers, anodes, cathode materials using the composition provided herein. Suitable formulations may consist of 1 mg/mL purified SWNT, mixed with 5 wt % cyclic triterpenoid in $H_2O$ solvent, and combined with a degassed terpene at 1:1 ratio each, and mixed with polymer and electrolyte such as, but not limited to, acid doped polyaniline, with organic sulfonic acid based dopant of molecular weight greater than 22,000 that is at least 1-35 weight % with preferred 10-20 weight %. The formulation may be used in ink for jetting, stamping, printing, coating, and dipping, onto substrates including but not limited to glass, metal, electrodes, or dielectrics leading to enhanced electrochemical, dielectric, electro-optical properties.

Compositions with enhanced electric, optical, and thermal properties such that film, ink, paint, or dye media ensues are provided herein. The formulations of the compositions may include a solute of 1 mg/mL non-functionalized graphene, mixed with a 5 weight % cyclic triterpenoid in $H_2O$ solvent such that vacuum filtration using a factor of at least 30 with porous alumina membrane (pore size~200 nm), leaves a homogenous thin-film, that is dry transferred and patterned using tape transfer and lithography, onto an adhesive media, such as, but not limited to, APTES adhesive coated ITO glass, or semiconductive polymer substrate, such as but not limited to polythiophene.

A composition of nanostructured material that can undergo hydrogenation which produces a hydrogen storage and trapping media with release at 50-100° C., and/or where oxygenation produces superconductive properties, such that temperature, and liquid and gas, or supercritical-based type hydrogenations or oxygenation at moderate pressures of at least 4 MPa. The formulation comprises a 20 mg/mL sublimed fullerene solute that is mixed with a terpene solvent, and combined with metal catalysts with respective ordered mesoporous materials, such as, but not limited to nanostructured sonochemical Zn with Pd and Pt (0.1 to 20% by weight), at Pt—Pd:Zn of 2:3 ratio with respective ordered mesoporous material, such as, but not limited to aluminum oxide, magnesia support and mesoporous hydrothermal calcinied SBA-15 (Pluronic P123 template). This formulation produces a thermal-electrical fluid, gel, lubricant, film, or media such that at least 83% by weight of solution and at last 17% by weight of catalyst which consists of at least 1 weight % Pt and at least 4.5-5.5 weight % Pd and at least 6.75-8.25% weight Zn on 85.5% by weight of mesoporous support.

A composition for enhanced electric or thermal properties results in anti-cancer, anti-viral, anti-fungal drug delivery properties. The formulation comprises at least 20 mg/mL purified solute of sublimed fullerene mixed with a terpene solvent leading to a drug delivery or skin permeable agent such as film, fluid, lubricant, or gel which can increase skin permeability. The formulation has enhanced electrical and thermal skin conductivity, prevents the binding of virus, bacteria, and fungus and thereby prevents penetration, and/or the development of infection.

A composition of nanostructured material capable of producing a thermal-electrical fluid, gel, lubricant, film, or media. The formulation consisting of 20 mg/mL sublimed fullerene solute that is mixed with a terpene solvent, and combined with metal catalysts and respective ordered mesoporous materials, such as, but not limited to, nanostructure sonochemical catalyst with at least 1 weight % Pt and at least 4.5-5.5 weight % Pd and at least 6.75-8.25% weight Zn on respective ordered mesoporous material, such as, but not limited to aluminum oxide, magnesia support and mesoporous hydrothermal calcinied SBA-15 (Pluronic P123 template) using a Pt—Pd:Zn ration of 2:3.

What is claimed is:
1. A method for producing solutions or colloids comprising allotropes of carbon, the method comprising:
combining an allotrope of carbon selected from the group consisting of a fullerene, graphene, or a single walled carbon nanotube with a solvent selected from the group consisting of 1,4 cineole, 1,8 cineole, linalool, oleyl alcohol, alpha-terpinene, gamma-dodecalactone, and gamma-octalactone to produce a solution or colloid,
wherein the solution or colloid comprises 1 mg/mL to 100 mg/mL of the carbon allotrope.

2. The method of claim 1, further comprising:
processing the solution or colloid by cavitation.

3. The method of claim 1, further comprising:
ultracentrifuging the solution or colloid to yield a supernatant that is characterized as a true solution of the carbon allotrope; and
characterizing the solution with photoluminescence or other optical spectroscopy.

4. The method of claim 1, further comprising combining the solution with media selected from the group consisting of degassed solvent, fluid, feel, additive, lubricant, polymer, film, gel, electrolyte, mesoporous material, metal catalyst, fillers, adhesive, paint, ink, dye, or substrate media to yield a film, gel, grease, coating, biofuel, gasoline fuel, kerosene, identification dyes, detergents, surfactants, degassed solvents, corrosion inhibitors, biofuel additives, engine oil additives, antifriction agents, antiwear agents, oil misting additives, synthetic additives, gel additives, grease additives, oil, grease, gel, oil misting lubricants, synthetic oil, synthetic based grease, synthetic based gel, turbocharger lubricant, supercharger lubricant, low temperature heat transfer fluid, heat pump fluid, phase-change fluid, solar collector fluid, parabolic trough fluid, power plant fluid, electrical-thermal energy storage fluids, anti-freeze fluids, industrial heat transfer fluids, conductive polymer, semiconductive polymers, polymer fluids, polymer films, polymer thin films, polymer gels, dye-sensitized fluids, electrolytes, or dye-sensitized electrolytes.

\* \* \* \* \*